United States Patent [19]
Lynch et al.

[11] 4,179,504
[45] Dec. 18, 1979

[54] ALKYL AMINE OXIDE TOXICANTS

[75] Inventors: Donald M. Lynch, Waldwick; Myron J. Lover, Mountainside; Arnold J. Singer, South Orange; William E. Rhodes, III, Cranford, all of N.J.

[73] Assignee: Block Drug Company, Inc., Jersey City, N.J.

[21] Appl. No.: 842,057

[22] Filed: Oct. 14, 1977

[51] Int. Cl.² ............................................ A61K 31/535
[52] U.S. Cl. ............................. 424/248.4; 424/248.57
[58] Field of Search ................. 424/248.57, 325, 248.4

[56] References Cited
U.S. PATENT DOCUMENTS
3,484,523  12/1969  Findlan .............................. 424/325

OTHER PUBLICATIONS
Passedouet et al. — Chem. Abst., vol. 75, (1971) p. 121,397s.

Primary Examiner—Sam Rosen
Attorney, Agent, or Firm—Ostrolenk, Faber, Gerb & Soffen

[57] ABSTRACT

Alkyl amine oxides have been found to exhibit valuable insecticidal and/or ovicidal activity.

8 Claims, No Drawings

ALKYL AMINE OXIDE TOXICANTS

BACKGROUND OF THE INVENTION

A great number of insecticidal toxicants are known today. However, because of increased concern about the overall safety of some of the known ectoparasitic toxicants, the search for new, safe and effective materials has intensified recently.

Many species of insects encase their ova in protective sheaths which are impregnable to most toxicants. The developmental period of the egg is often relatively long in comparison to the life cycle of the adult forms. In such cases, an agent effective only against the adults must persist for the lifetime of the developing ovum or must be reapplied as successive hatchings occur.

Few, if any, of the ectoparasitic toxicants in commercial use contribute to produce performance, but must be supported by extraneous components for emulsifying, foaming or cleansing purposes.

It has now been found that alkyl amine oxides are effective ectoparasiticidal and/or ovicidal toxicants. These compounds are known materials and have heretofore been employed in various cleansing and degerming compositions for their emulsifying properties. Some of the myriad compositions are set forth in U.S. Pat. Nos. 3,296,145, 3,484,523, 3,929,990 and 3,943,234. One commercial shampoo formulation contains 1% N-stearyl-N,N-dimethylamine oxide, and another commercial shampoo contains 2% N-myristyl-N,N-dimethylamine oxide. U.S. Pat. No. 4,033,895 discloses a shampoo containing 4–18 parts sodium lauryl sulfate, 0.1–4 parts zinc pyridinethione and 0.2–12 parts N-stearyl-N,N-dimethyl amine oxide.

It is the object of this invention to provide new, safe and effective toxicants for ectoparasites and their ova. It is the further object of this invention to provide insect toxicants which have intrinsic emulsifying, foaming and cleansing properties. They may be used alone as primary active ingredients, or in combination with other toxicants in which the alkyl amine oxides contribute insecticidal and/or ovicidal power while providing valuable secondary properties to the compositions. This and other objects of the invention will become apparent to those skilled in the art from the following detailed description.

SUMMARY OF THE INVENTION

This invention relates to ectoparasiticidal toxicants and a method of controlling ectoparasites. More particularly, the invention relates to the use of alkyl amine oxides as toxicants for ectoparasites and/or their ova and to toxicant compositions containing such oxides as toxicants and adjunctives and emulsifiers, foaming agents and cleansers.

DESCRIPTION OF THE PREFERRED EMBODIMENTS

The toxicants of the instant invention are alkyl amne oxides of the formula

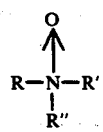

in which R is alkyl, alkenyl or alkylamidoalkyl of 8 to 20 carbon atoms and in which R and R' are individually lower alkyl, hydroxy lower alkyl or are linked to complete a heterocyclic radical such as morpholine. Typical examples of the oxides of the instant invention include: N-lauryl-N,N-dimethylamine oxide, N-myristyl-N,N-dimethylamine oxide, N-coco-N,N-dimethylamine oxide, N-cocomorpholine dimethylamine oxide, N-stearyl-N,N-dimethylamine oxide, N-hydrogenated tallow-N,N-dimethylamine oxide, N-tallow-N,N-bis-(2-hydroxyethyl)-amine oxide, and N-cocoamidopropyl-N,N-dimethylamine oxide.

One or more of the toxic oxides of the present invention can be incorporated into an active toxicant composition which can be in the form of a liquid, powder, lotion, cream, gel or aerosol spray, or foam as the result of formulation with inert pharmaceutically acceptable carries by procedures well known in the art. Of particular interest is the application to shampoo and body wash products, where all of the attributes of skin mildness, foaming propensities, detergency and insecticidal activity coalesce. Any pharmaceutically acceptable carrier, whether aqueous or not aqueous, which is inert to the active ingredient can be employed. By inert is meant that the carrier does not have a substantial detrimental effect on the insecticidal or ovicidal toxicant activity of the active ingredient. The formulations should not contain a strong detergent. For example, the shampoo of the aforementioned U.S. Pat. No. 4,033,895 does not contain an effective toxic amount of the alkyl amine oxide, as defined herein, because of the presence of the sodium lauryl sulfate, which tends to remove the active residue which would otherwise containue to act on the lice or their ova.

The active oxides are incorporated into the toxicant composition used to treat the animal or human host in need of such treatment, believed to be in need of such treatment, or desired to be prophylactically protected in an effective toxicant amount. By such amount is meant the amount which will cause at least 50% of the ectoparasites to die within 24 hours in the case of ectoparasites and within two weeks in the case of ova. The minimum concentration of oxide required to provide an effective toxic amount varies considerably depending on the particular oxide, the particular inert pharmaceutically acceptable carrier being employed and any other ingredients which are present. Thus, in one case a 10% concentration may suffice, while in other cases, concentrations as high as 40% may be required to obtain an effective toxic dose. Usually, the oxides will be present in concentrations of about 1 to 25% and most preferably in concentrations of about 10 to 20%.

The instant oxides can also be employed as an adjunct toxicant in a preparation which otherwise exhibits insecticidal and/or ovicidal activity. In such preparations, the term "effective toxic dose" means that amount which will increase the mortality rate by at least about 20%.

A particularly desirable component in the compositions of this invention is one or more $C_{1-18}$ aliphatic alcohols such as ethanol, isopropanol, pentanol, hexadecyl alcohol and the like in an amount of about 5–90%, preferably about 20–30%. The alcohol enhances the activity of the toxicant to a high degree.

When the ectoparasite is the human body louse, the standard mortality tests are the following two minute immersion tests:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed on a 2×2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4×4 cm black corduroy cloth path and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lice are then removed and the number of plump, viable eggs and shriveled non-fertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion tests, controls are run in identical manners to that described, with room temperature (24° C.) tap water substituted for the sample to be tested. The results of the tests reported are net results.

For determining miticidal activity, the following procedure is used:

Into a one cubic foot chamber, held at room temperature, is placed a covered microscope depression slide containing ten adult mixed sex mites, *Psoroptes equi.* var. cuniculi. The slide is positioned at a distance of ten inches horizontally and four inches below the activator of a mechanical spray device and uncovered. The mechanical pump spray device delivers 50 milligrams of sample per depression of the activator. The sample to be tested, maintained at room temperature, is shaken until homogeneous and placed in the mechanical pump spray device. The primed activator is depressed twice, releasing 100 milligrams of spray mist into the closed chamber. The mist is allowed to settle and the slide containing the mites is removed and covered. This point of time is considered zero hours. The covered slide is then held at room temperature for 24 hours. Microscopic observations are noted at 0, 1, 3, and 24 hours post treatment. Controls are run in an identical manner as that described using water or the diluting agent, and net mortality results are reported.

The pediculicidal and ovicidal activity of various toxicants of the instant invention were tested in the two minute immersion tests described above. The concentration of oxide which caused 50% mortality ($LC_{50}$) and which caused 99% mortality ($LC_{99}$) was determined in a system where the oxide was mixed with 25% isopropanol and water q.s. The results are shown in the following table:

| Compound | Pediculicidal | | Ovicidal | |
| --- | --- | --- | --- | --- |
| | $LC_{99}$ | $LC_{50}$ | $LC_{99}$ | $LC_{50}$ |
| N-Decyl-N,N-dimethylamine oxide | — | >30 | — | >30 |
| N-Lauryl-N,N-dimethylamine oxide | — | >30 | — | >30 |
| N-Myristyl-N,N-dimethylamine oxide | — | >30 | >30 | 28 |
| N-Coco-N,N-dimethylamine oxide | — | >30 | — | >30 |
| N-Cocomorpholine oxide | — | >30 | — | >30 |
| N-Stearyl-N,N-dimethylamine oxide | 15 | 7.7 | 6.6 | 3.5 |
| N-Hydrogenated tallow-N,N-dimethylamine oxide | >30 | 27 | 9 | 6.9 |
| N-Tallow-N,N-bis-(2-hydroxyethyl)-amine oxide | >30 | 19 | 4.5 | 2.9 |
| N-Cocoamidopropyl-N,N-dimethylamine oxide | — | >30 | — | >30 |
| N-Hexadecyl-N,N-dimethylamine oxide | >30 | 22.4 | >40 | 36 |
| N-Oleyl-N,N-dimethylamine oxide | 28 | 19.6 | 20 | 12 |

It will be seen from the foregoing table that the stearyl amine oxide was the most effective pediculicidal and ovicidal toxicant and that the tallow and hydrogenated tallow amine oxides also provided excellent results.

The pediculicidal and ovicidal activity of the stearyl amine oxide as a function of concentration was determined in the standard two minute tests described above in a system containing 25% isopropanol and water q.s. The results were:

| Concentration | % Pediculicidal Mortality | % Ovicidal Mortality |
| --- | --- | --- |
| 1 | 10 | 12 |
| 3 | 20 | 35 |
| 5 | 35 | 95 |
| 7 | 40 | 98 |
| 9 | 35 | 100 |
| 11 | 60 | 100 |
| 15 | 95 | 100 |
| 15 | 100 | * |

*NOT TESTED

The miticidal activity of the instant oxides was determined and the 24 hour results after treatment with a solution containing 15% by weight of the amine oxide, 25% isopropanol and 60% water were:

| Compound | % Mortality |
| --- | --- |
| N-Decyl-N,N-dimethylamine oxide | 100 |
| N-Lauryl-N,N-dimethylamine oxide | 100 |
| N-Myristyl-N,N-dimethylamine oxide | 100 |
| N-Coco-N,N-dimethylamine oxide | 100 |
| N-Cocomorpholine oxide | 100 |
| N-Stearyl-N,N-dimethylamine oxide | 60 |
| N-Hydrogenated tallow-N,N-dimethylamine oxide | 100 |
| N-Tallow-N,N-bis-(2-hydroxyethyl)-amine oxide | 30 |
| N-Cocoamidopropyl-N,N-dimethylamine oxide | 90 |
| N-Hexadecyl-N,N-dimethylamine oxide | 60 |
| N-Oleyl-N,N-dimethylamine oxide | 100 |

The following Table shows the pediculicidal effect of the lower alkanol on a system containing N-stearyl-N,N-dimethylamine oxide (SAO), triethanolamine lauryl sulfate (TEALS), isopropanol (IPA) and water q.s. ad. 100%.

| % TEALS | % SAO | % IPA | % Activity |
|---|---|---|---|
| 4 | 12 | 0 | 25 |
| 4 | 12 | 25 | 85 |
| 6 | 6 | 0 | 0 |
| 6 | 6 | 25 | 55 |
| 8 | 8 | 0 | 0 |
| 8 | 8 | 25 | 60 |
| 8 | 12 | 0 | 0 |
| 8 | 12 | 25 | 50 |
| 14 | 8 | 0 | 0 |
| 14 | 8 | 25 | 60 |
| 18 | 4 | 0 | 0 |
| 18 | 4 | 25 | 50 |

The following data shows the use of the alkyl amine oxides as an adjunct toxicant:

|  | % W/W | % Pediculicidal Mortality | % Ovicidal Mortality |
|---|---|---|---|
| N-Coco-$\beta$-aminopropionic acid | 20 | 100 | 28 |
| Water | 80 | | |
| pH 6.2 | | | |
| N-Coco-$\beta$-aminopropionic acid | 20 | 90 | 100 |
| N-Stearyl-N,N-dimethylamine oxide | 5 | | |
| Water | 75 | | |
| pH 7.1 | | | |

The following Table shows pediculicidal and ovicidal activity of N-stearyl-N,N-dimethylamine oxide (SAO) as a function of concentration in water:

| % SAO | % Pediculicidal Mortality | % Ovicidal Mortality |
|---|---|---|
| 15 | 35 | 100 |
| — | 10 | 100 |
| 11 | 5 | 97 |
| 9 | 0 | 91 |
| 7 | 0 | 100 |
| 5 | 0 | 100 |
| 3 | 0 | 66 |
| 1 | 0 | 5 |

The pediculicidal activity of 15% SAO, 25% alcohol and 60% water and that of 25% alcohol and 75% water was found to be:

| | % Mortality | |
| Alcohol | SAO/Alcohol/H$_2$O | Alcohol/H$_2$O |
|---|---|---|
| Methanol | 15 | 0 |
| Ethanol | 70 | 0 |
| Isopropanol | 100 | 0 |
| Isobutanol | 95 | 40 |
| Sec-Butanol | 100 | 0 |
| n-Butanol | 80 | 20 |
| n-Pentanol | 25 | 10 |
| n-Hexanol | 40 | 5 |
| Hexadecyl alcohol | 50 | 40 |

As noted above, various end use formulations can be prepared. Some typical formulations are set forth below and the amounts recited are percentages by weight:

| | % w/w |
|---|---|
| Clear liquid suitable for inunction or mechanical spray application | |
| N-Tallow-N,N-bis-(2-hydroxyethyl)-amine oxide | 40 |
| Isopropanol | 25 |
| Water | 35 |
| Shampoo | |
| N-Oleyl-N,N-Dimethylamine oxide | 30 |
| Ethanol | 25 |
| Triethanolamine lauryl sulfate | 17 |
| Water | 28 |
| Lotion | |
| N-Stearyl-N,N-dimethylamine oxide | 15 |
| Isopropanol | 25 |
| Xanthan Gum | 0.5 |
| Water | 59.5 |
| Miticidal Gel | |
| N-Myristyl-N,N-dimethylamine oxide | 15 |
| Isopropanol | 25 |
| Carboxypolymethylene | 0.5 |
| Triethanolamine | 0.5 |
| Water | 59 |
| Aerosol Foam | |
| N-Stearyl-N,N-dimethylamine oxide | 15 |
| Isopropanol | 19 |
| Glyceryl monostearate | 8 |
| Water | 50 |
| Isobutane | 8 |
| Stick | |
| N-Oleyl-N,N-dimethylamine oxide | 30 |
| Sodium stearate | 8 |
| Sorbitol | 3.5 |
| Ethanol | 49 |
| Water | 9.5 |
| Cream | |
| N-Stearyl-N,N-dimethylamine oxide | 15 |
| Isopropanol | 20 |
| Glyceryl monostearate | 8 |
| Sodium stearate | 2 |
| Water | 55 |

Various changes and modifications can be made in the present invention without departing from the spirit and scope thereof. The various embodiments described herein were for the purpose of illustration only and were not intended to limit the invention. Unless otherwise specified, all temperatures have been in degrees Centigrade and all parts and percentages by weight throughout this specification and claims.

We claim:

1. A method of controlling lice, mites or their ova which comprises applying to a human or an animal in need of such control, an effective toxic amount of at least one alkyl amine oxide wherein said oxide is of the formula

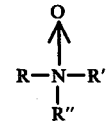

wherein R is alkyl, alkenyl or alkylaminoalkyl of 8 to 20 carbon atoms and R' and R" are individually selected from the group consisting of lower alkyl and hydroxy lower alkyl, or are linked so as to form with the nitrogen to which they are attached a morpholine group.

2. The method of claim 1 wherein said oxide is selected from the group consisting of N-lauryl-N,N-dimethylamine oxide, N-myristyl-N,N-dimethylamine oxide, N-coco-N,N-dimethylamine oxide, N-cocomorpholine oxide, N-hydrogenated tallow-N,N-dimethylamine oxide, N-tallow-N,N-bis-(2-hydroxyethyl)-amine oxide and N-cocoamidopropyl-N,N-dimethylamine oxide.

3. The method of claim 1 wherein said oxide is N-stearyl-N,N-dimethylamine oxide.

4. The method of claim 1 wherein said oxide is employed in combination with an inert pharmaceutically acceptable carrier.

5. The method of claim 4 wherein said carrier is aqueous.

6. The method of claim 1 wherein said alkyl amine oxide is employed in combination with an aliphatic alcohol.

7. The method of claim 6 wherein said alcohol is isopropanol.

8. The method of claim 7 wherein said oxide is employed in combination with an inert aqueous pharmaceutically acceptable carrier.

* * * * *